(12) United States Patent
Kang

(10) Patent No.: US 10,946,182 B2
(45) Date of Patent: Mar. 16, 2021

(54) SUBCUTANEOUS VEIN ACCESS PORT AND MEDICINE INJECTION DEVICE HAVING THE SAME

(71) Applicant: MEDI TULIP CO., LTD., Cheongju-si (KR)

(72) Inventor: Min Woong Kang, Daejeon (KR)

(73) Assignee: MEDI TULIP CO., LTD., Cheongju-si (KR)

(*) Notice: Subject to any disclaimer, the term of this patent is extended or adjusted under 35 U.S.C. 154(b) by 119 days.

(21) Appl. No.: 16/310,449

(22) PCT Filed: Mar. 5, 2018

(86) PCT No.: PCT/KR2018/002561
§ 371 (c)(1),
(2) Date: Dec. 17, 2018

(87) PCT Pub. No.: WO2018/164422
PCT Pub. Date: Sep. 13, 2018

(65) Prior Publication Data
US 2019/0329015 A1    Oct. 31, 2019

(30) Foreign Application Priority Data
Mar. 7, 2017    (KR) .......................... 10-2017-0028941

(51) Int. Cl.
*A61M 39/02*    (2006.01)
*A61M 5/142*    (2006.01)

(52) U.S. Cl.
CPC .... *A61M 39/0208* (2013.01); *A61M 5/14276* (2013.01); *A61M 39/0247* (2013.01);
(Continued)

(58) Field of Classification Search
CPC ...... A61M 39/0208; A61M 2039/0238; A61M 5/427; A61M 2205/587
See application file for complete search history.

(56) References Cited

U.S. PATENT DOCUMENTS

| 2004/0199220 A1 | 10/2004 | Cantlon |
| 2007/0078391 A1 | 4/2007 | Wortley et al. |

(Continued)

FOREIGN PATENT DOCUMENTS

| EP | 2856965 A1 | 4/2015 |
| JP | 07-255847 A | 10/1995 |

(Continued)

OTHER PUBLICATIONS

International Search Report for PCT/KR2018/002561 dated Jun. 27, 2018 from Korean Intellectual Property Office.

*Primary Examiner* — Emily L Schmidt
(74) *Attorney, Agent, or Firm* — Revolution IP, PLLC

(57) ABSTRACT

A subcutaneous vein access port implanted into a living body to be connected to a subcutaneous vein, includes: a housing formed therein with a receiving portion to which a medicine is supplied; a cover membrane disposed at an upper end of the housing and sealing an upper side of the receiving portion; a conduit provided to the housing and inserted into the subcutaneous vein to connect the subcutaneous vein to the receiving portion; and a light source emitting light such that the light from the light source is discharged outside through the cover membrane.

7 Claims, 7 Drawing Sheets

(52) U.S. Cl.
CPC ............... *A61M 2039/027* (2013.01); *A61M 2039/0238* (2013.01); *A61M 2039/0258* (2013.01); *A61M 2039/0261* (2013.01)

(56) References Cited

U.S. PATENT DOCUMENTS

| | | |
|---|---|---|
| 2009/0105688 A1 | 4/2009 | McIntyre et al. |
| 2009/0192493 A1 | 7/2009 | Meng et al. |
| 2010/0268165 A1* | 10/2010 | Maniar ............. A61M 39/0208 604/175 |
| 2013/0289482 A1 | 10/2013 | Meng et al. |
| 2015/0297115 A1 | 10/2015 | Babu |

FOREIGN PATENT DOCUMENTS

| | | |
|---|---|---|
| JP | 2014-028145 A | 2/2014 |
| KR | 10-2014-0091062 A | 7/2014 |
| KR | 10-2016-0069181 A | 6/2016 |
| WO | 2007/126645 A2 | 11/2007 |
| WO | 2011-034529 A1 | 3/2011 |

* cited by examiner

[FIG. 1]
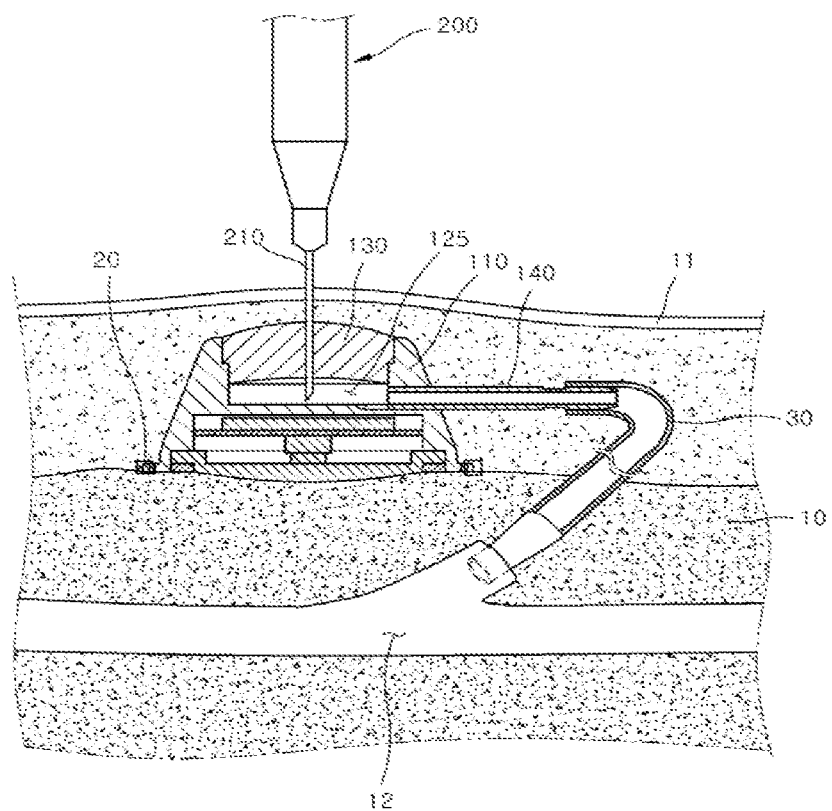
[FIG. 2]
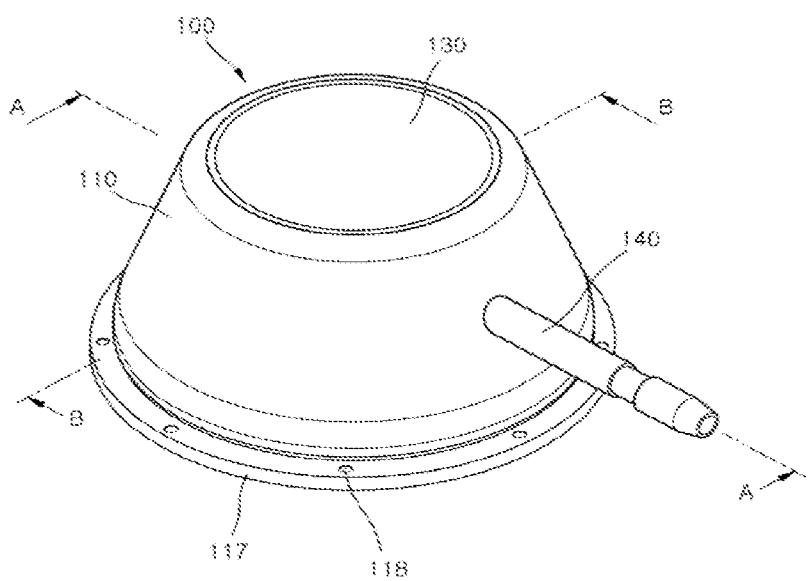

[FIG. 3]
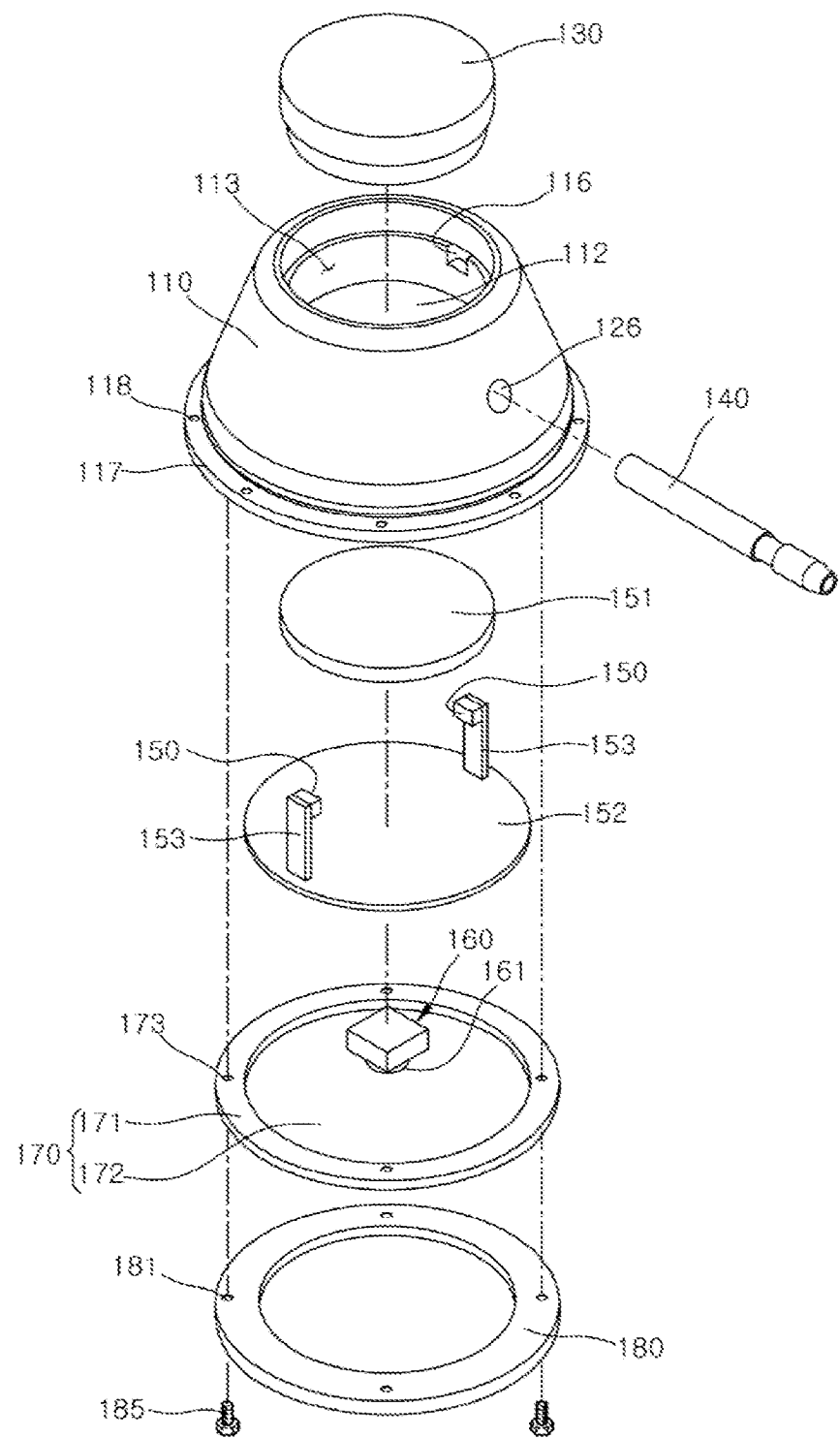

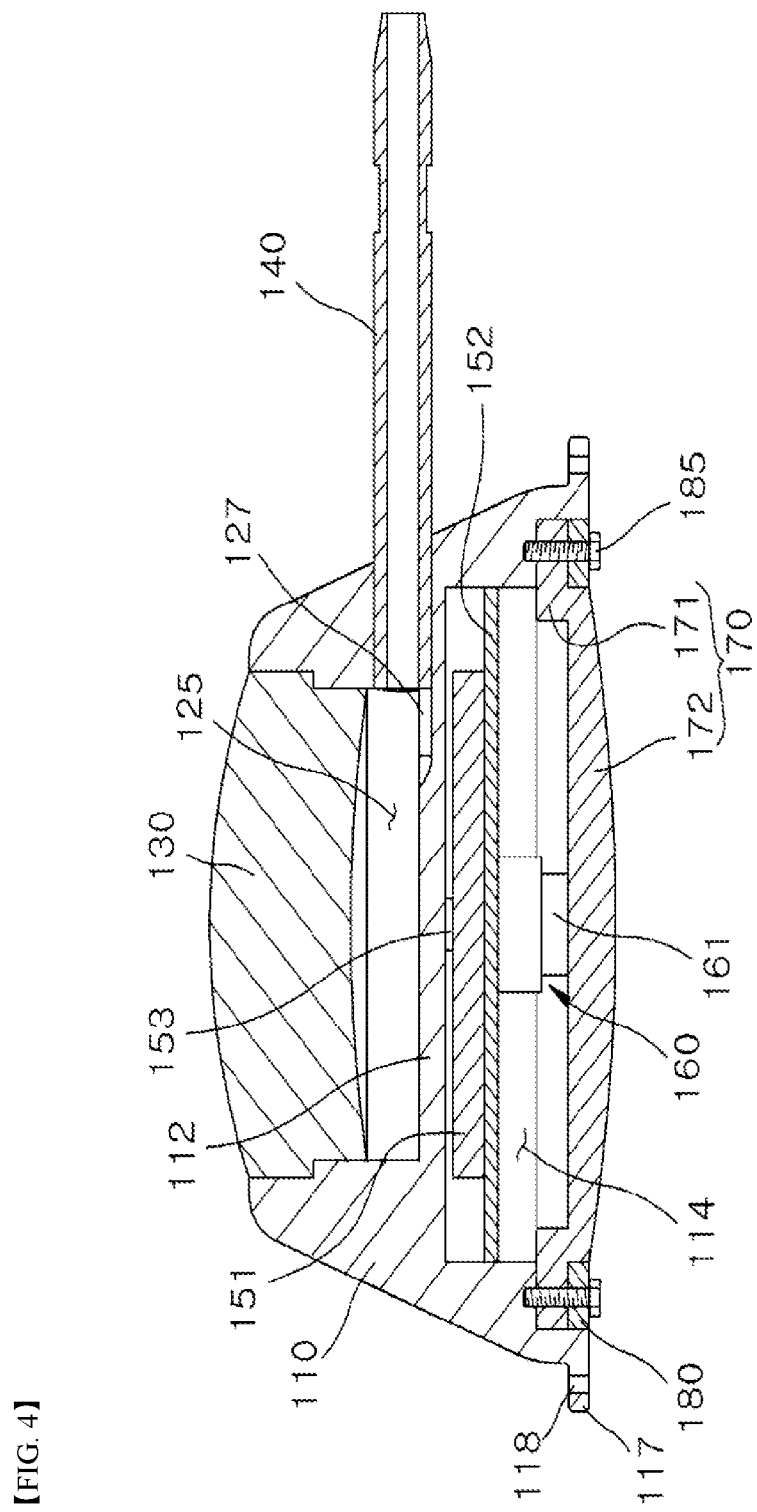
[FIG. 4]

【FIG. 5】
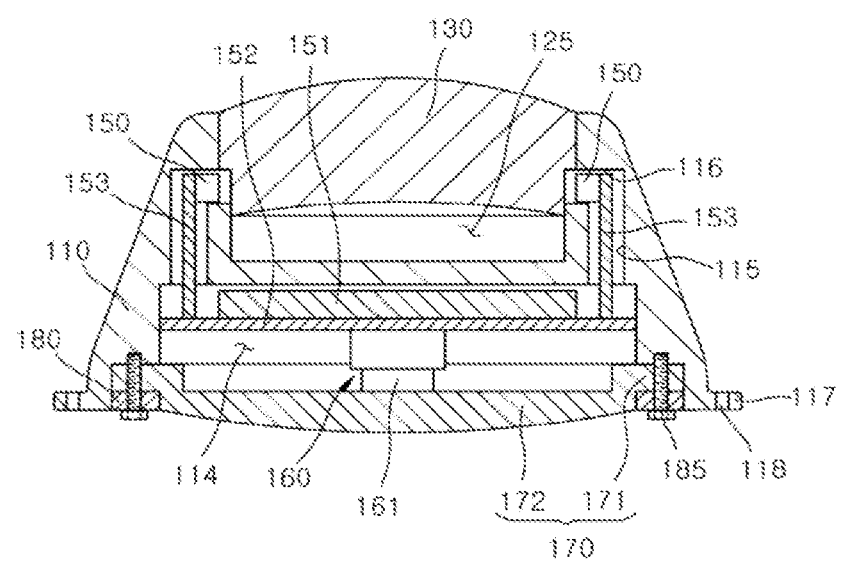

[FIG. 6]
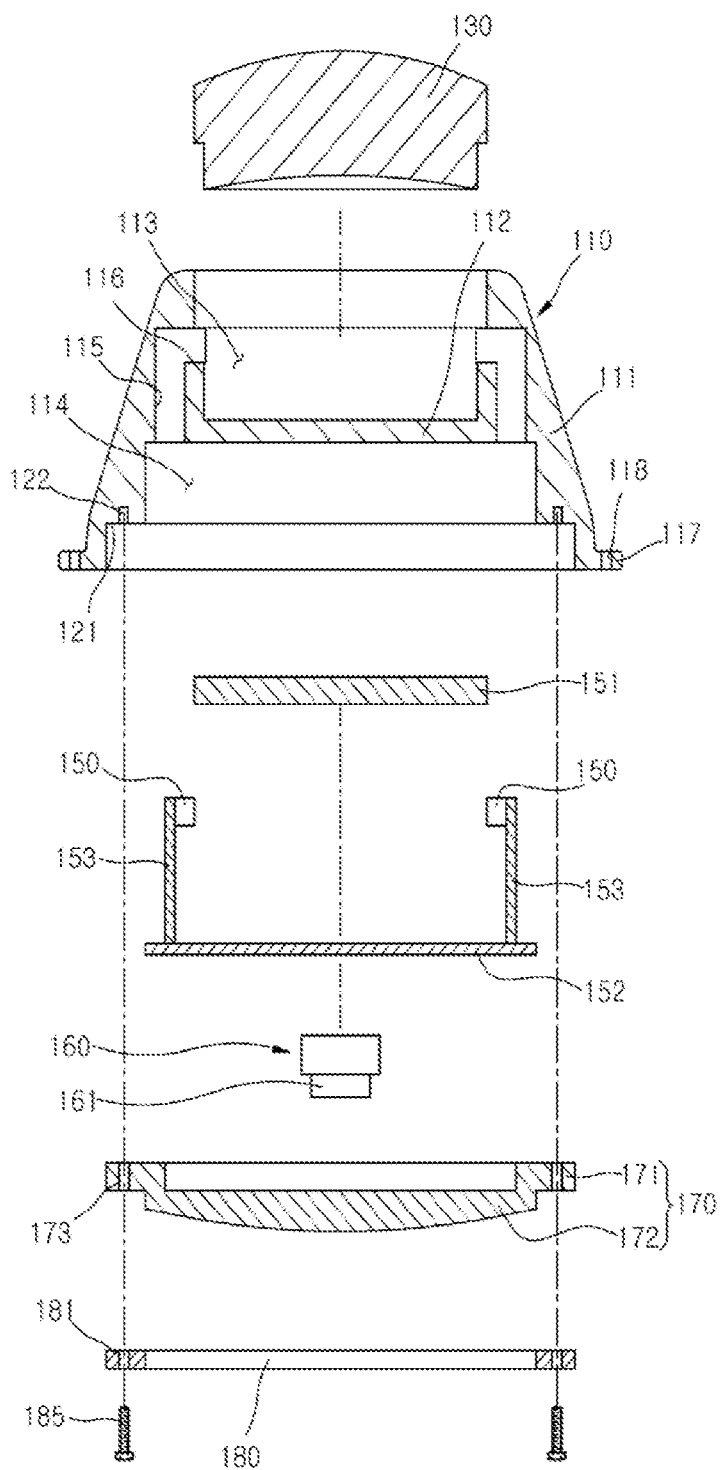

【FIG. 7】
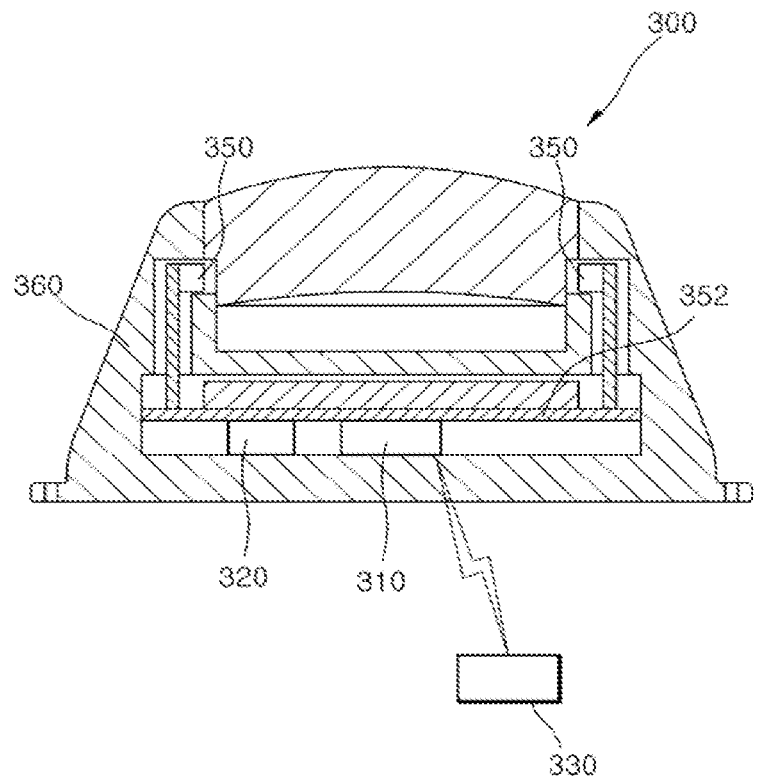
【FIG. 8】
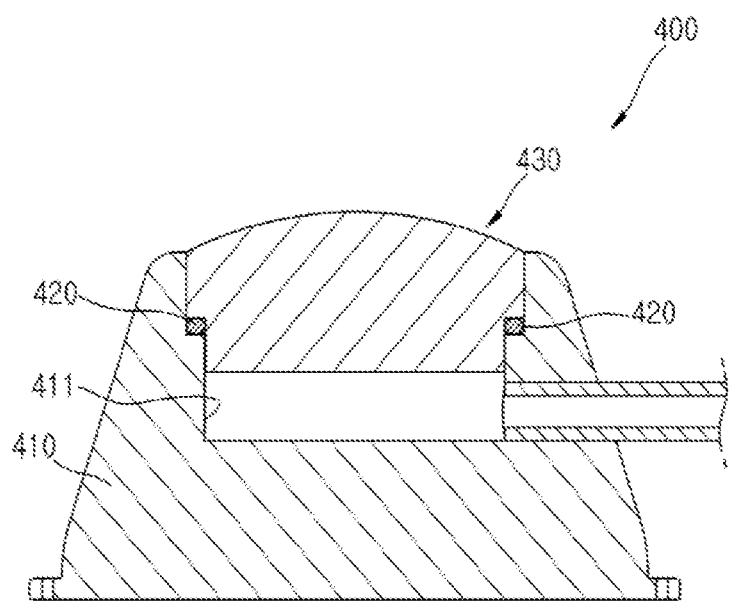

【FIG. 9】
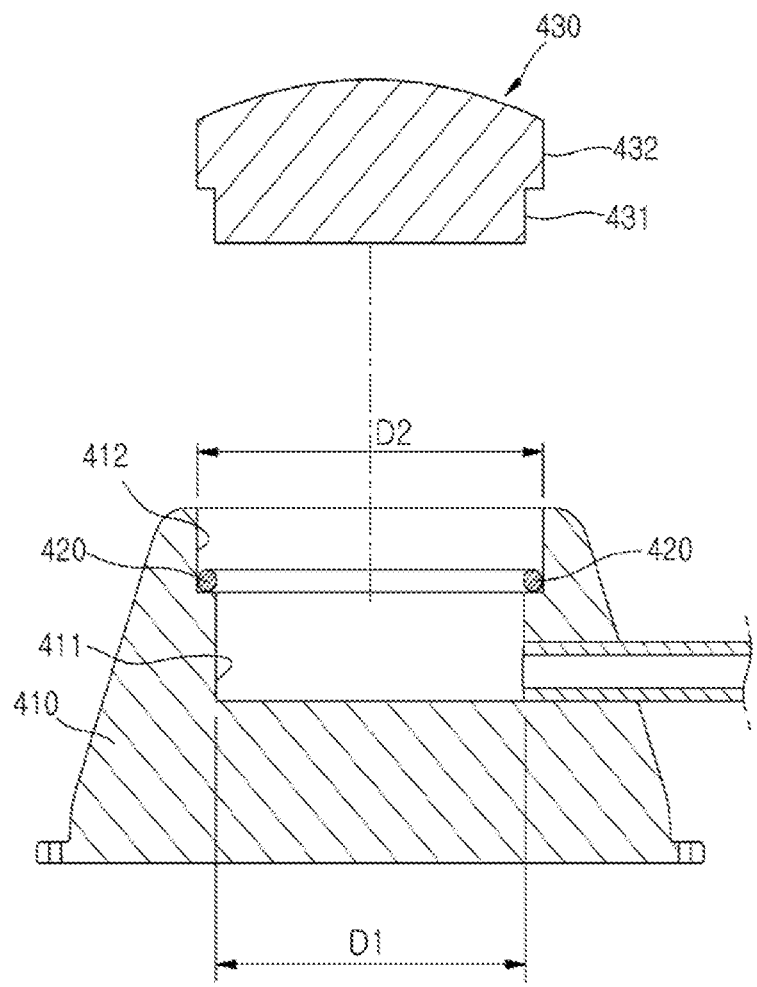

SUBCUTANEOUS VEIN ACCESS PORT AND MEDICINE INJECTION DEVICE HAVING THE SAME

TECHNICAL FIELD

The present invention relates to a subcutaneous vein access port and a medicine injection device including the same and, more particularly, to a subcutaneous vein access port which is easy to locate after being implanted into the human body, and a medicine injection device including the same.

BACKGROUND ART

A subcutaneous vein access port is a device adapted to be implanted into the human body for administration of a medicine, such as an anticancer agent, or blood transfusion and collection.

Generally, such a subcutaneous vein access port is used for patients requiring intermittent or continuous infusion of anticancer agents, antibiotics, blood products, parenteral nutritional supplements, Ringer's solutions, or analgesics, patients whose peripheral blood vessels are difficult to detect, and patients requiring long-term treatment at home or in a hospital. Advantageously, the subcutaneous vein access port is invisible from outside, does not require disinfection when not in use, allows a patient to swim or bathe, and has a long service life of several months to several years.

A typical medicine injection device includes a chamber implanted into the human body and adapted to receive a medicine supplied from outside and a catheter connecting the chamber to the subcutaneous vein. Here, the chamber is sealed with a self-sealing cover membrane and the medicine is supplied to the chamber through a syringe needle penetrating the cover membrane.

In a process of injecting a medicine into the implanted chamber, an operator usually visually identifies the location of the implanted chamber, holds the periphery of the chamber with their free hand, and sticks the needle into the cover membrane based on an estimated location of the cover membrane. However, since the implanted chamber is hidden by the skin, it is not easy to identify an exact location of the chamber with the naked eye. In addition, since the cover membrane is smaller than the chamber and has a small area to be stuck by the needle, it is difficult for an unskilled person to insert the needle into the cover membrane with accuracy and safety.

Therefore, there is a need for a subcutaneous vein access port which allows an exact location of a cover membrane to be easily identified from outside.

One example of the background technique is disclosed in Korean Patent Publication No. 2014-0091062 (published Jul. 18, 2014).

DISCLOSURE

Technical Problem

It is an aspect of the present invention to provide a subcutaneous vein access port which is easy to locate after being implanted into the human body, and a medicine injection device including the same.

The above and other aspects of the present invention will become apparent to those skilled in the art from the detailed description of the following embodiments in conjunction with the accompanying drawings.

Technical Solution

In accordance with one aspect of the present invention, a subcutaneous vein access port implanted into a living body to be connected to a subcutaneous vein includes: a housing formed therein with a receiving portion to which a medicine is supplied; a cover membrane disposed at an upper end of the housing and sealing an upper side of the receiving portion; a conduit provided to the housing and inserted into the subcutaneous vein to connect the subcutaneous vein to the receiving portion; and a light source emitting light such that the light from the light source is discharged outside through the cover membrane.

In one embodiment, the subcutaneous vein access port may further include: a power supply disposed in the housing; and a substrate disposed in the housing and electrically connecting the power supply to the light source.

In one embodiment, the housing may include: a body formed therethrough with a coupling hole to which the conduit is connected; and a partition dividing an interior of the body into a first space and a second space, and the light source is disposed on an inner circumferential surface of the first space and emits light toward the cover membrane such that the light exits the cover membrane through an upper surface of the cover membrane.

In one embodiment, the body may have: a first through-hole extending from an upper side of the second space inside the body in a vertical direction; and a second through-hole connected to the first through-hole and extending to the inner circumferential surface of the first space.

In one embodiment, the subcutaneous vein access port may further include: a support inserted into the first through-hole, wherein the support is electrically connected at a lower end thereof to the substrate and is provided at an upper end thereof with the light source disposed in the second through-hole to allow electricity to be delivered to the light source from the power supply through the support.

In one embodiment, the subcutaneous vein access port may further include: a switch disposed under the substrate and comprising a push portion, the switch allowing electricity to be supplied to the light source when the push portion is pressed while allowing electricity supply to the light source to be stopped when the push portion is released; and an actuator allowing the push portion to be selectively pressed to turn the switch on/off.

In one embodiment, the actuator may include: a sealing portion tightly contacting a mounting groove circumferentially formed in a stepped manner at a lower end of the body; and a pressing portion connected to the sealing portion to seal the second space, wherein the pressing portion is adapted to be elastically deformed upward to press the push portion and to be elastically deformed downward to release the push portion to turn the switch on/off.

In one embodiment, the subcutaneous vein access port may further include a securing ring pressing the entirety of the sealing portion to secure the actuator to the body.

In one embodiment, the subcutaneous vein access port may further include: a plurality of first coupling holes formed in the mounting groove in a circumferential direction thereof; a plurality of second coupling holes formed through the sealing portion to correspond to the first coupling holes; a plurality of third coupling holes formed through the securing ring to correspond to the second coupling holes; and a fastening member driven into the third coupling hole to be coupled to the first coupling hole through the second coupling hole to secure the actuator and the securing ring to the body.

In one embodiment, the subcutaneous vein access port may further include: a receiver disposed on the substrate and receiving an operation signal from an external transmitter; and a controller disposed on the substrate and controlling the light source to emit light when the receiver receives the operation signal.

In one embodiment, the light source may be a chemiluminescent light source disposed between an inner circumferential surface of the housing and the cover membrane and emitting light toward the cover membrane when pressed by the cover membrane.

In one embodiment, the housing may include a first inner circumferential portion having a first diameter and a second inner circumferential portion having a second diameter greater than the first diameter and formed in a stepped manner on the first inner circumferential portion; the light source may be disposed on an upper side of the first inner circumferential portion; and the cover membrane may include a first cover portion coupled to the first inner circumferential portion and a second cover portion formed on the first cover portion and coupled to the second inner circumferential portion, wherein the second cover may be elastically deformed to press the light source when pressed.

In accordance with another aspect of the present invention, a medicine injection device includes: the subcutaneous vein access port set forth above; and a syringe including a needle, wherein the needle penetrates the cover membrane of the subcutaneous vein access port to allow the medicine to be injected into the receiving portion therethrough.

Advantageous Effects

A subcutaneous vein access port according to the present invention includes a light source, wherein light from the light source is discharged to the outside through a cover membrane, whereby the location of the cover membrane can be easily identified with the naked eye from the outside.

In addition, light can be emitted from the light source by a simple operation of depressing the subcutaneous vein access port, thereby allowing quick identification of the location of the cover membrane.

Further, the subcutaneous vein access port includes a receiver, such that the light source can emit light when the receiver receives an operation signal from an external transmitter.

Moreover, the light source is formed of a chemiluminescent material that emits light when pressed from the outside, whereby light can be emitted from the light source by a simple operation of depressing the subcutaneous vein access port.

It should be understood that the effects of the present invention are not limited to those described above, and include all effects that can be deduced from features of the invention set forth in the following detailed description or the appended claims.

DESCRIPTION OF DRAWINGS

FIG. 1 is a schematic view of a medicine injection device according to a first embodiment of the present invention.

FIG. 2 is a perspective view of a subcutaneous vein access port according to a first embodiment of the present invention.

FIG. 3 is an exploded perspective view of the subcutaneous vein access port according to the first embodiment.

FIG. 4 is a sectional view taken along line A-A of FIG. 2.

FIG. 5 is a sectional view taken along line B-B of FIG. 2.

FIG. 6 is an exploded sectional view of the subcutaneous vein access port according to the first embodiment.

FIG. 7 is a schematic sectional view of a subcutaneous vein access port according to a second embodiment of the present invention.

FIG. 8 is a schematic sectional view of a subcutaneous vein access port according to a third embodiment of the present invention.

FIG. 9 is a schematic exploded sectional view of the subcutaneous vein access port according to the third embodiment.

BEST MODE

Hereinafter, embodiments of the present invention will be described with reference to the accompanying drawings. It should be understood that the present invention may be embodied in different ways and is not limited to the following embodiments. In the drawings, portions irrelevant to the description will be omitted for clarity. Like components will be denoted by like reference numerals throughout the specification.

When an element or layer is referred to as being "on," "connected to," or "coupled to" another element or layer, it may be directly on, connected to, or coupled to the other element or layer or intervening elements or layers may be present. In addition, when an element or layer is referred to as "comprising" a certain component, it may further include one or more other components unless otherwise stated.

The terminology used herein is for the purpose of describing particular embodiments and is not intended to be limiting. As used herein, the singular forms "a", "an" and "the" are intended to include the plural forms as well, unless the context clearly indicates otherwise. It will be further understood that the terms "comprise(s)" and/or "comprising," when used in this specification, specify the presence of stated features, steps, operations, elements, and/or components, but do not preclude the presence or addition of one or more other features, steps, operations, elements, components, and/or groups.

Hereinafter, embodiments of the present invention will be described with reference to the accompanying drawings.

FIG. 1 is a schematic view of a medicine injection device according to a first embodiment of the present invention.

Referring to FIG. 1, the medicine injection device may include: a subcutaneous vein access port 100 and a syringe 200. The subcutaneous vein access port 100 may be implanted into a living body. The subcutaneous vein access port 100 may be secured to human tissue, for example, the fascia 10. The subcutaneous vein access port 100 may be firmly secured to the human tissue by a suture 20.

The syringe 200 may include a needle 210 inserted through skin 11 and a cover membrane 130 of the subcutaneous vein access port 100, wherein the needle 210 allows a medicine to be supplied to a receiving portion 125 of the subcutaneous vein access port 100 therethrough. The receiving portion 125 may be connected to the subcutaneous vein 12 through a conduit 140 and a tube 30 of the subcutaneous vein access port 100 such that the medicine in the receiving portion 125 can be supplied to the subcutaneous vein 12 via the conduit 140 and the tube 30.

FIG. 2 is a perspective view of a subcutaneous vein access port according to a first embodiment of the present invention, FIG. 3 is an exploded perspective view of the subcutaneous vein access port, FIG. 4 is a sectional view taken along line A-A of FIG. 2, FIG. 5 is a sectional view taken along line B-B of FIG. 2, and FIG. 6 is an exploded sectional view of the subcutaneous vein access port.

Referring to FIG. 2 to FIG. 6, a subcutaneous vein access port 100 according to this embodiment may include a housing 110, a cover membrane 130, a conduit 140, and a light source 150.

The housing 110 may include a body 111 and a partition 112.

The body 111 may define a contour of the housing 110 and may have an axial space therein.

The partition 112 may be disposed horizontally with respect to the body 111 and may divide an interior of the body 111 into a first space 113 and a second space 114. Referring to FIG. 6, the first space 113 may be defined above the partition 112 and the second space 114 may be defined below the partition 112.

In addition, the body 111 may have a first through-hole 115 extending from an upper side of the second space 114 inside the body 111 in the vertical direction. Further, the body 111 may have a second through-hole 116 connected to the first through-hole 115 and extending to an inner circumferential surface of the first space 113.

The body 111 may include a flange 117 outside a lower end thereof, wherein the flange 117 may have a plurality of through-holes 118 formed at predetermined intervals in a circumferential direction thereof. A suture 20 as described above (FIG. 1) may be coupled to the through-holes 118.

The body 111 may include a mounting groove 121 formed inside the lower end thereof. The mounting groove 121 may be formed in a stepped manner in the circumferential direction of the body 111. In addition, a plurality of first coupling holes 122 may be formed in the mounting groove 121 in the circumferential direction thereof.

The cover membrane 130 may be coupled to the first space 113 to seal an upper side of the first space 113. In addition, the cover membrane 130 may be coupled to upper and middle sections of the first space 113 such that the second through-hole 116 can be sealed by the cover membrane 130. With the cover membrane 130 coupled to the first space 113, a lower section of the first space 113 is an empty space, which may constitute a receiving portion 125 adapted to receive a medicine supplied through a needle 210 (FIG. 1). That is, the receiving portion 125 may be a space defined by the first space 113 and a lower surface of the cover membrane 130 coupled to the first space 113. Since an upper side of the receiving portion 125 and the second through hole 116 are sealed by the cover membrane 130, the medicine supplied to the receiving portion 125 can be stably received in the receiving portion 125.

The cover membrane 130 can be self-sealed and may be formed of any suitable self-sealing material, without limitation. For example, the cover membrane 130 may be formed of an elastomer, such as silicone, silicone rubber, or latex.

In addition, the cover membrane 130 may have a convex upper surface. With this shape, an operator can easily depress the subcutaneous vein access port 100.

The conduit 140 may be provided to the housing 110 and may be inserted into the subcutaneous vein 12 (FIG. 1) to connect the subcutaneous vein 12 to the receiving portion 125. Here, the conduit 140 may directly connect the housing 110 to the subcutaneous vein 12 or may indirectly connect the housing 110 to the subcutaneous vein 12 via a separate tube 30 (FIG. 1).

The body 111 may be formed therethrough with a coupling hole 126 to which the conduit 140 is connected. The coupling hole 126 may be formed horizontally with respect to the body 111 to be connected to the first space 113. In addition, the partition 112 may have a groove 127 formed on a bottom surface thereof to be connected to the coupling hole 126. Here, the groove 127 may have a diameter corresponding to the diameter of the coupling hole 126. Accordingly, the conduit 140 coupled to the coupling hole 126 can be smoothly connected to the receiving portion 125 through the groove 127, whereby partial blockage of the conduit 140 by the partition 112 can be prevented, thereby preventing increase in conduit resistance. In this way, the medicine supplied to the receiving portion 125 can be effectively introduced into the conduit 140 through the groove 127 of the partition 112.

The light source 150 may emit light to outside through the cover membrane 130. In addition, the light source 150 may be disposed on the inner circumferential surface of the first space 113. Specifically, the light source 150 may emit light toward the cover membrane 130 and the light from the light source 150 may exit the cover membrane 130 through the upper surface of the cover membrane 130. The cover membrane 130 may be formed of a light transmissive material to allow light from the light source 150 to be discharged therethrough.

In addition, the subcutaneous vein access port 100 may further include a power supply 151 and a substrate 152.

The power supply 151 may be disposed in the housing 110. Specifically, the power supply 151 may be disposed in the second space 114 of the housing 110. The power supply 151 may supply electric power to the light source 150.

The substrate 152 may be disposed in the housing 110 to electrically connect the power supply 151 to the light source 150. The substrate 152 may be disposed in the second space 114 of the housing 110. The substrate 152 may be a printed circuit board (PCB).

In addition, the subcutaneous vein access port 100 may include a support 153. The support 153 may be inserted into the first through-hole 115 and may be electrically connected at a lower end thereof to the substrate 152 and the light source 150 may be disposed at an upper end of the support 153 to be located in the second through-hole 116. Electric power from the power supply 151 may be delivered to the light source 150 through the support 153, such that the light source 150 can emit light. Light from the light source 150 enters the cover membrane 130 through a side surface of the cover membrane 130, passes through the inside of the cover membrane 130, and exits the cover membrane 130 through the upper surface of the cover membrane 130. The support 153 may be a printed circuit board (PCB) or a flexible printed circuit board (FPCB), and the light source may be an LED.

The first through-hole 115 may include a plurality of first through-holes 115, and the same applies to the second through-hole 116, the support 153, and the light source 150. Here, the plurality first through-holes 115 may be arranged symmetrical to one another around the central axis of the subcutaneous vein access port 100 or may be arranged at predetermined angle intervals in the circumferential direction, and the same applies to a plurality of second through-holes 116, a plurality of supports 153, and a plurality of light sources 150. Accordingly, light discharged through the cover membrane 130 upon operation of the light source 150 can correspond in shape to the upper surface or contour of the cover membrane 130, as viewed from the outside of the skin.

In this way, an operator can easily and accurately recognize the location of the cover membrane 130.

The light source 150 may be disposed in the second through-hole 116 so as not to protrude from the second through-hole 116. In this way, the cover membrane 130 can be easily coupled to the housing 110 without causing damage to the light source 150.

In addition, the subcutaneous vein access port 100 may further include a switch 160, an actuator 170, and a securing ring 180.

The switch 160 may be disposed under the substrate 152. In addition, the switch 160 may include a push portion 161. The switch 160 may be adapted to allow electric power to be supplied to the light source 150 when the push portion 161 is pushed and to allow power supply to the light source 150 to be stopped when the push portion 161 is released. The switch 160 may be a tact switch, without being limited thereto.

The actuator 170 may include a sealing portion 171 and a pressing portion 172. The sealing portion 171 may be inserted into and pressed against the mounting groove 121 circumferentially formed in a stepped manner at the lower end of the body 111. The sealing portion 171 may have second coupling holes 173 formed therethrough to correspond to the first coupling holes 122 formed in the mounting groove 121.

The pressing portion 172 may be connected to the sealing portion 171 to seal the second space 114. The pressing portion 172 may be adapted to be elastically deformed. Specifically, the pressing portion 172 may be elastically deformed upward to press the push portion 161 and may be elastically deformed downward to allow the push portion 161 to be released therefrom. That is, the push portion 161 may be selectively pressed by the underlying actuator 170 to turn the switch 160 on/off. The actuator 170 may be formed of an elastomer, such as silicon, silicone rubber, or latex, or a metal, such as a titanium sheet.

In addition, the pressing portion 172 may have a convex lower surface. With this shape, when an operator depresses the subcutaneous vein access port 100, the pressing portion 172 can be easily pressed by the human tissue to which the subcutaneous vein access port 100 is provided.

When an operator depresses the cover membrane 130 with the subcutaneous vein access port 100 implanted into a living body, the pressing portion 172 may be elastically deformed upward by being pressed by the human tissue to which the subcutaneous vein access port 100 is secured. As the pressing portion 172 is elastically deformed upward to press the push portion 161 of the switch 160, the switch 160 is turned on to allow electric power to be supplied to the light source 150 from the power supply 151 such that light source 150 emits light. That is, according to the present invention, an operator can quickly and easily recognize the location of the cover membrane 130 by a simple operation of depressing the subcutaneous vein access port 100 as needed. After administration of the medicine is completed, the operator may depress the subcutaneous vein access port 100 again such that the pressing portion 172 can press the push portion 161 again to stop power supply to the light source 150 to turn off the light source 150.

The securing ring 180 may press the entirety of the sealing portion 171 to secure the actuator 170 to the body 111. The securing ring 180 may have third coupling holes 181 formed therethrough to correspond to the second coupling holes 173 of the sealing portion 171. The securing ring 180 may be formed of a metal to provide sufficient strength.

A fastening member 185 may be driven into the third coupling hole 181 to be coupled to the first coupling hole 122 through the second coupling hole 173. In this way, the actuator 170 and the securing ring 180 can be firmly coupled to the body 111.

FIG. 7 is a schematic sectional view of a subcutaneous vein access port according to a second embodiment of the present invention. A subcutaneous vein access port according to this embodiment differs from the subcutaneous vein access port according to the first embodiment in terms of a mechanism for supplying electric power to a light source. Since the rest of the subcutaneous vein access port according to this embodiment is substantially the same as that of the subcutaneous vein access port according to the first embodiment, detailed description thereof will be omitted.

Referring to FIG. 7, a subcutaneous vein access port 300 according to this embodiment may further include a receiver 310 and a controller 320.

The receiver 310 may be disposed on a substrate 352 to receive an operation signal from an external transmitter 330. The receiver 310 may communicate a signal such as an ultrasonic wave signal or an infrared (IR) signal.

The controller 320 may be disposed on the substrate 352 and allows a light source 350 to be powered and emit light when the receiver 310 receives an operation signal having information causing the light source 350 to emit light. In addition, the controller 320 may control a switch (not shown) to stop power supply to the light source 350 when the receiver 310 receives an operation signal having information causing the light source 350 to stop emitting light.

In this embodiment, the actuator 170 and the securing ring 180 described in the first embodiment may be omitted and a body 360 may be closed at a lower end thereof.

FIG. 8 is a schematic sectional view of a subcutaneous vein access port according to a third embodiment of the present invention and FIG. 9 is a schematic exploded sectional view of the subcutaneous vein access port.

Referring to FIG. 8 and FIG. 9, for a subcutaneous vein access port 400 according to this embodiment, a housing 410 may have a first inner circumferential portion 411 having a first diameter D1 and a second inner circumferential portion 412 having a second diameter D2 greater than the first diameter D1 and formed in a stepped manner on the first inner circumferential portion 411.

In addition, a light source 420 may be disposed on an upper side of the first inner circumferential portion 411.

A cover membrane 430 includes a first cover portion 431 coupled to the first inner circumferential portion 411 and a second cover portion 432 formed on the first cover portion 431 and coupled to the second inner circumferential portion 412.

With the cover membrane 430 coupled to the housing 410, the light source 420 may be located between an inner circumferential surface of the housing 410 and the cover membrane 430. Specifically, the light source 420 may be located between the upper side of the first inner circumferential portion 411 and a lower portion of the second cover portion 432. When the cover membrane 430 coupled to the housing 410 is depressed by external force, the light source can be depressed by the second cover portion 432 elastically deformed to emit light. In addition, the light from the light source 420 enters the cover membrane through a side surface of the first cover portion 431 and a lower surface of the second cover portion 432 and then is discharged through an upper surface of the second cover portion 432. Here, the light source 420 may be a chemiluminescent light source that emits light when pressed by external force.

While certain embodiments have been described, these embodiments have been presented by way of example only, and are not intended to limit the scope of the disclosures. Indeed, the embodiments described herein may be embodied in a variety of other forms. Furthermore, various omissions, substitutions and changes in the form of the embodiments described herein may be made without departing from the spirit of the disclosure. For example, features described as being implemented alone may also be implemented in combination thereof, and vice versa.

The accompanying claims and their equivalents are intended to cover such forms or modifications as would fall within the scope and spirit of the disclosure.

INDUSTRIAL APPLICABILITY

The subcutaneous vein access port according to the present invention allows location of a cover membrane, through which a syringe needle passes, to be easily identified with the naked eye from outside, and thus can be used as a subcutaneous vein access port for patients requiring intermittent or continuous infusion of anticancer agents, antibiotics, blood products, parenteral nutritional supplements, Ringer's solutions, or analgesics, patients whose peripheral blood vessels are difficult to detect, and patients requiring long-term treatment at home or in a hospital.

The invention claimed is:

1. A subcutaneous vein access port comprising:
a housing formed therein with a receiving portion to which a medicine is supplied;
a cover membrane disposed at an upper end of the housing and sealing an upper side of the receiving portion;
a conduit provided to the housing and connected to the receiving portion;
a light source emitting light such that the light from the light source is discharged outside through the cover membrane;
a power supply disposed in the housing;
a substrate disposed in the housing and electrically connecting the power supply to the light source, wherein the power supply is positioned on the substrate;
a switch disposed under the substrate and comprising a push portion, the switch allowing electricity to be supplied to the light source when the push portion is pressed while allowing electricity supply to the light source to be stopped when the push portion is released; and
an actuator directly contacting the push portion to be selectively pressed to turn the switch on/off,
wherein the housing comprises a body formed therethrough with a coupling hole to which the conduit is connected; and a partition dividing an interior of the body into a first space and a second space,
wherein the first space is defined above the partition and the second space is defined below the partition,
the receiving portion is a space defined by the first space and a lower surface of the cover membrane,
the power supply and the substrate are disposed in the second space,
wherein the actuator comprises a sealing portion tightly contacting a mounting groove circumferentially formed in a stepped manner at a lower end of the body, and a pressing portion connected to the sealing portion to seal the second space,
wherein the subcutaneous vein access port further comprises:
a securing ring being inserted into the mounting groove and pressing the entirety of the sealing portion to secure the actuator to the body;
a plurality of first coupling holes formed in the mounting groove in a circumferential direction thereof;
a plurality of second coupling holes formed through the sealing portion to correspond to the first coupling holes;
a plurality of third coupling holes formed through the securing ring to correspond to the second coupling holes; and
a fastening member driven into the third coupling hole to be coupled to the first coupling hole through the second coupling hole to secure the actuator and the securing ring to the body.

2. The subcutaneous vein access port according to claim 1,
wherein the partition has a groove to be connected to the coupling hole.

3. The subcutaneous vein access port according to claim 1, wherein the light source is disposed on an inner circumferential surface of the first space and emits light toward the cover membrane such that the light exits the cover membrane through an upper surface of the cover membrane.

4. The subcutaneous vein access port according to claim 3, wherein the body has: a first through-hole extending from an upper side of the second space inside the body in a vertical direction; and a second through-hole connected to the first through-hole and extending to the inner circumferential surface of the first space.

5. The subcutaneous vein access port according to claim 4, further comprising:
a support inserted into the first through-hole,
wherein the support is electrically connected at a lower end thereof to the substrate and is provided at an upper end thereof with the light source disposed in the second through-hole to allow electricity to be delivered to the light source from the power supply through the support.

6. The subcutaneous vein access port according to claim 1, wherein
the pressing portion is adapted to be elastically deformed upward to press the push portion and to be elastically deformed downward to allow the push portion to be released therefrom to turn the switch on/off.

7. A medicine injection device comprising:
the subcutaneous vein access port according to claim 1; and
a syringe comprising a needle, the needle penetrating the cover membrane of the subcutaneous vein access port to allow the medicine to be injected into the receiving portion therethrough.

* * * * *